United States Patent [19]

Bollinger et al.

[11] 4,086,078

[45] Apr. 25, 1978

[54] USE OF PYRIDYL PHTHALAMIC ACIDS AS PLANT GROWTH REGULANTS

[75] Inventors: Frederic G. Bollinger; John J. D'Amico, both of St. Louis, Mo.

[73] Assignee: Monsanto Company, St. Louis, Mo.

[21] Appl. No.: 753,393

[22] Filed: Dec. 22, 1976

[51] Int. Cl.$^2$ ............................................. A01N 9/22
[52] U.S. Cl. ........................................ 71/94; 71/76
[58] Field of Search ...................................... 71/94, 76

[56] References Cited

U.S. PATENT DOCUMENTS 3,549,348  12/1970  Gevirtz et al. ...................... 71/94 X
3,658,892  4/1972  Martin et al. ................. 260/518 A X

OTHER PUBLICATIONS

Hoffman et al., Science, vol. 109 (1949), p. 588.
Teubner et al., Science, vol. 122 (1955), p. 74.
Cooper et al., J. Chem. Soc. (1971), p. 3257.

*Primary Examiner*—Lewis Gotts
*Assistant Examiner*—Catherine L. Mills
*Attorney, Agent, or Firm*—Richard H. Shear; Donald W. Peterson

[57] ABSTRACT

Certain pyridyl phthalamic acids have been found to be effective in regulating the growth of leguminous plants.

2 Claims, No Drawings

USE OF PYRIDYL PHTHALAMIC ACIDS AS PLANT GROWTH REGULANTS

The invention relates to a method of regulating the natural growth or development of plants by means of a chemical treatment. More specifically, the invention is directed to a method whereby the natural growth or development of leguminous plants is regulated by applying to said plants a compound having the formula

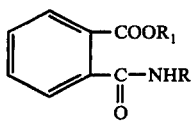

wherein R is pyridyl or pyridyl substituted by halo or alkoxy having from one to four carbon atoms; $R_1$ is hydrogen, lower alkyl and agriculturally acceptable cations.

As used herein, the term "agriculturally acceptable cations" includes those cations which are commonly used in plant growth regulating compositions to form the salt of the free acid, including but not limited to substituted amine, such as isopropylamine and triethylamine, ammonium and alkali metal cations.

As used herein, the regulation of "plant growth or development" is understood to mean the modification of the normal sequential development of a treated plant to agricultural maturity. Such modifications are most readily observed as changes in size, shape, color or texture of the treated plant or any of its parts. Similarly, changes in the quantity of plant fruit or flowers are also quite apparent from visual inspection. The above changes may be characterized as an acceleration or retardation of plant growth, stature reduction, leaf or canopy alteration, increased branching, terminal inhibition, increased flowering, defoliation, increased root growth, increased cold hardiness and the like. While many of these modifications are desirable in and of themselves, most often it is their effect on the economic result that is of most importance. For example, a reduction in stature of the plant permits the growing of more plants per unit area. A darkening of the foliar color is illustrative of higher chloryphyll activity indicative of improved rate of photosynthesis.

Although phytotoxic amounts of the active ingredient may be employed to exert a herbicidal effect, the regulation of plant growth in accordance with the present invention does not include the total inhibition or killing of such plants. The present invention contemplates the use of an amount of active ingredient which will modify the normal sequential development of the treated plant to agricultural maturity. Such plant growth regulating amounts may vary, not only with the material selected, but also with the modifying effect desired, the species of plant and its stage of development, the plant growth medium and whether a permanent or a transitory effect is sought. It is, however, well within the skill of the art to determine the amount of active ingredient required.

Modification of the plants may be accomplished by applying the active ingredient to seeds, emerging seedlings, roots, stems, leaves, flowers, fruits or other plant parts. Such application may be made directly to the plant part, or indirectly by application to the plant growth medium.

By the term "active ingredient" is meant the active pyridyl phthalamic acids of the above formula. As an illustration of active ingredients useful in accordance with the present invention, the following examples are presented.

EXAMPLE 1

To a stirred slurry containing 0.1 moles of phthalic anhydride and 150 ml. of chloroform, 0.1 moles of 2-amino-4-chloropyridine was added in one portion. The reaction mixture was stirred at 25°–30° C. for 24 hours. The precipitate was collected by filtration, air-dried at 25°–30° C. and identified as N-(5-chloro-2-pyridyl)phthalamic acid having a melting point of 177°–178° C. (% yield = 85)

Anal. Calc'd. Cl, 12.81; N, 10.12 Found Cl, 12.78; N, 10.29.

EXAMPLE 2

To a stirred slurry containing 0.1 moles of phthalic anhydride and 100 ml. of chloroform, 0.1 moles of 3-amino-2-chloropyridine was added in one portion. The reaction mixture was stirred for 24 hours. The precipitate was filtered, air-dried and identified as N-(2-chloro-3-pyridyl)phthalamic acid having a melting point of 203° C. (% yield = 87)

Anal. Calc'd. Cl, 12.81; N, 10.12 Found Cl, 12.94; N, 10.37.

EXAMPLE 3

To a stirred slurry containing 0.1 moles of phthalic anhydride and 175 ml. of chloroform, 0.1 moles of 5-amino-2-methoxypyridine was added in one portion. The reaction mixture was stirred at 25°–30° C. for 24 hours. The precipitate was collected by filtration, air-dried and identified as N-(6-methoxy-3-pyridyl)phthalamic acid having a melting point of 228°–229° C. (% yield = 99)

Anal. Calc'd. C, 61.80; H, 4.44; N, 10.30 Found C, 61.94; H, 4.42; N, 10.26.

EXAMPLE 4

To a stirred slurry containing 0.1 moles of phthalic anhydride and 100 ml. of chloroform, 0.1 moles of 2-amino-5-bromopyridine was added in one portion. After stirring for 24 hours at 25°–30° C., the precipitate was collected by filtration, air-dried and identified as N-(5-bromo-2-pyridyl)phthalamic acid having a melting point of 183°–184° C. (% yield = 85)

Anal. Calc'd. C, 48.62; H, 2.82; N, 8.72 Found C, 48.73; H, 2.07; N, 8.63.

EXAMPLE 5

The sodium salt of N-(5-chloro-2-pyridyl)phthalamic acid is prepared by adding a stoichiometrically equivalent amount of 50% aqueous NaOH and 400 ml. water for a 0.1 mole reaction. After stirring for three hours, the impurities may be removed by filtration.

Alakli metal salts of other pyridyl phthalamic acids may be prepared in a similar manner. Ammonium and substituted amine salts may be prepared in accordance with the following example.

EXAMPLE 6

To a stirred slurry of 0.1 moles of N-(5-chloro-2-pyridyl)phthalamic acid and 500 ml. of ethyl ether, 0.11 moles of isopropylamine, to form the isopropylamine salt, was added in one portion. After stirring at 25°-30° C. for 24 hours, a solid was collected by filtration and air-dried. The product, mp 147°-148° C., was obtained in 100% yield.

Anal. Calc'd. C, 57.23; H, 5.40; Cl, 10.56; N, 12.61 Found C, 57.30; H, 5.34; Cl, 10.53; N, 12.41.

EXAMPLE 7

To a stirred slurry containing 27.7 grams (0.1 moles) of N-(2-chloro-3-pyridyl)phthalamic acid and 300 ml. of methyl alcohol, 71 grams (0.5 moles) of boron trifluoride etherate $[(C_2H_5)_2O.BF_3]$ is added in one portion. An exothermic reaction set in causing a temperature rise from 21°-33° C. The stirred mixture is heated at reflux for 24 hours. After cooling to $-10°$ C., 1000 ml. of a 10% aqueous sodium bicarbonate solution is added slowly at $-10°$ to 0° C. After stirring at 0° to 10° C. for 30 minutes, the solid is collected by filtration, washed with water until neutral and air-dried at 25°-30° C. The product, mp 110°-112° C., is obtained in 76% yield. After two recrystallizations from heptane/isopropyl alcohol, it melted at 122°-124° C.

Anal. Calc'd. for $C_{14}H_{11}ClN_2O_3$: C, 57.84; H, 3.81; Cl, 12.20; N, 9.64 Found: C, 57.88; H, 3.57; Cl, 12.45; N, 9.41.

In the practice of the invention, the active ingredient can be used alone or in combination with a material referred to in the art as an adjuvant in either liquid or solid form. To prepare plant growth regulating compositions, the active ingredient is admixed with an adjuvant including diluents, extenders, carriers and conditioning agents to provide compositions in the form of finely-divided particulate solids, granules, pellets, wettable powders, dusts, solutions and aqueous dispersions or emulsions. Thus, the active ingredient can be used with an adjuvant such as a finely-divided particulate solid, a solvent liquid of organic origin, water, a wetting agent, dispersing agent or emulsifying agent or any suitable combination of these.

Illustrative finely-divided solid carriers and extenders which are useful in plant growth regulating compositions of this invention include the talcs, clays, pumice, silica, diatomaceous earth, quartz, Fullers earth, sulfur, powdered cork, powdered wood, walnut four, chalk, tobacco dust, charcoal and the like. Typical liquid diluents include Stoddard solvent, acetone, alcohols, glycols, ethyl acetate, benzene and the like. The plant growth regulating compositions of this invention, particularly liquids and wettable powders, usually contain one or more surface-active agents in amounts sufficient to render a given composition readily dispersible in water or in oil. The term "surface-active agent" is understood to include wetting agents, dispersing agents, suspending agents and emulsifying agents. Such surface-active agents are well-known and reference is made to U.S. Pat. No. 2,547,724, Columns 3 and 4, for detailed examples of the same.

Generally, the active ingredients are applied in the form of a composition containing one or more adjuvants which aid in the application of a uniform distribution of the active ingredient. The application of liquid and particulate solid compositions of the active ingredient can be carried out by conventional techniques utilizing for example, spreaders, power dusters, boom and hand sprayers and spray dusters. The compositions can also be applied from airplanes as a dust or spray. Should the application of the plant growth composition to the plant growth medium be desired, this is accomplished by incorporating the compositions in the soil or other media in the area where modifications of the plants is desired.

Compositions of this invention generally contain from about 5 to 95 parts active ingredient, about 1 to 50 parts surface active agent and about 4 to 94 parts solvent, all parts being by weight based on the total weight of the composition.

In selecting the appropriate rate of application of the active ingredient, it will be recognized that precise rates will also be dependent upon the mode of application, such as soil incorporation, band application, pre-plant seed treatment and various other factors known to those skilled in the art. In foliar treatment for the regulation of plant growth, the active ingredients are applied in amounts of from about 0.05 to about 10 or more pounds per acre. Preferred are foliar applications of from 0.05 to 5 pounds of the active ingredient per acre. In application to the soil habitat of germinant seeds, emerging seedlings and established vegetation for the regulation of plant growth, the active ingredients are applied in amounts of from 0.01 to about 20 pounds per acre or more. The application to the soil of from 0.1 to about 10 pounds of active ingredient per acre is preferred. Foliar application to plants beginning to blossom are preferred over other types of applications.

In accordance with the present invention, the compounds of the invention are found to be effective growth regulators for leguminous plants, as represented by soybean (Glycine max). Significant differences between those legumes treated with the active ingredient and those not treated are found to occur. Among the differences found are a reduction in stature of the treated legume, an alteration in canopy shape and a deepening of the foliar color. Other differences include inhibition of leaf size and axillary bud development. By reducing the stature of the plant, the growing energy utilized by the plant is directed more toward fruiting and less toward vegetation growth. This causes an increase in the plant's efficiency of production as well as an increase in the number of plants per unit area providing for an optimization of crop output. Further, shorter plants undergo less lodging. Thus, when harvested, less plants are lost and the yield is increased. Generally, plants of reduced stature tend to be more vigorous due to a greater tolerance to drought and cold.

In accordance with the practice of the invention, several plant growth regulating compositions were formulated utilizing various pyridyl phthalamic acid compounds as the active ingredient. These compositions were formulated so that they could be applied in tests at a rate the equivalent of 200 gallons per acre. Table I illustrates the formulation of the composition for several application rates of active ingredient. In each formulation, the stock solution utilized is 1% of the active ingredient dissolved in acetone.

Table I

| RATE Lbs/Acre (kilos/hectare) | ml. of 1% Stock Solution | ml. Acetone | ml. 0.39% TWEEN 20 in Water As Surfactant |
|---|---|---|---|
| 6.0 (6.72) | 2.0 | — | 3.6 |
| 5.0 (5.60) | 2.0 | 1.0 | 3.7 |
| 3.0 (3.36) | 1.0 | 1.0 | 3.6 |
| 2.5 (2.80) | 1.0 | 2.0 | 3.7 |
| 1.2 (1.34) | 0.4 | 1.6 | 3.6 |
| 1.0 (1.12) | 0.4 | 2.6 | 3.7 |
| 0.6 (.672) | 0.2 | 1.8 | 3.6 |
| 0.5 (.560) | 0.2 | 2.8 | 3.7 |

Table I-continued

| RATE Lbs/Acre (kilos/hectare) | ml. of 1% Stock Solution | ml. Acetone | ml. 0.39% TWEEN 20 in Water As Surfactant |
|---|---|---|---|
| 0.3 (.336) | 0.1 | 1.9 | 3.6 |

Utilizing compositions formulated in accordance with Table I, several compounds exhibited unexpected plant growth regulatory properties as illustrated by the test set forth in Example 8.

EXAMPLE 8

A number of soybean plants, variety Corsoy, are grown from seeds in aluminum pans in the greenhouse for a period of approximately one week to the primary leaf stage. The plants are thinned to three uniform plants in each pan and the height of each plant in the pan is measured to the terminal bud and the average height is noted. One pan containing three soybean plants is used for each chemical treatment and three pans are not treated and used as a control. The composition as formulated in accordance with Table I is then applied to the pan of growing plants by overhead spray at a rate equivalent to the desired rate of active ingredient per acre. The treated pans, along with the control pans, are maintained in a greenhouse and watered from below on a sand bench and fertilized with a uniform portion of a water-soluble balanced fertilizer.

Two weeks after application of the chemical, the average height of the soybean plants in the treated pan is again measured as above and the difference in the average height before and two weeks after application represent the increase in the development of the treated pans. This development in growth of the treated plants is compared to the average increase in growth of the plants in the control pans during the same period of time. A variation of 25% or more in the development of at least two-thirds of the treated plants when compared to the development of the control plants demonstrates that the chemical is an effective plant regulant. Thus, a chemical is considered active when the treated plants manifest a decrease in growth of at least 25% less than that of the control plants, i.e., stature reduction, or an increase in growth in excess of 25% of that of the control plants, i.e., growth stimulation.

Table II below summarizes the results and observations made in accordance with Example 8 when the pyridyl phthalamic acids of the invention were utilized as the active ingredient at several rates. Some slight phytotoxicity was noted, especially at the higher application rates.

Table II

| Compounds of Example | RATE Lbs/Acre (kilos/hectare) | Response |
|---|---|---|
| 1 | 6.0 (6.72) | Stature reduction, axillary bud development, leaf inhibition |
| 2 | 6.0 (6.72) | Stature reduction, axillary bud development, rosette growth |
|  | 3.0 (3.36) | Stature reduction, axillary bud development, rosette growth, leaf inhibition |
|  | 1.2 (1.34) | Stature reduction, axillary bud development, rosette growth, leaf inhibition |
|  | 0.6 (.672) | Stature reduction, axillary bud development, rosette growth |
| 3 | 6.0 (6.72) | Stature reduction, axillary bud development, leaf alteration, altered canopy, inhibition of apical development, slight leaf burn |
|  | 3.0 (3.36) | Stature reduction, axillary bud development, leaf alteration, altered canopy, slight leaf burn |
|  | 1.2 (1.34) | Stature reduction, axillary bud development, leaf distortion, altered canopy, slight leaf burn |
|  | 0.6 (.672) | Altered canopy, axillary bud development, slight leaf burn |
| 4 | 6.0 (6.72) | Stature reduction, axillary bud development, leaf inhibition, rosette growth, slight leaf burn |
|  | 3.0 (3.36) | Stature reduction, stem distortion, leaf inhibition, axillary bud development, rosette growth, slight leaf burn |
|  | 1.2 (1.34) | Stature reduction, axillary bud development, leaf inhibition, rosette growth |
| 5 | 6.0 (6.72) | Stature reduction, axillary bud development, rosette growth, slight leaf burn |
|  | 3.0 (3.36) | Stature reduction, axillary bud development, rosette growth |

Further advantages of this invention are shown in Example 9.

EXAMPLE 9

Individual soybean plants, variety Corsoy, are grown from seed in 6-inch pots containing a good grade of top soil. Two pots of 6-week old plants (5–6 trifoliate stage) are used for each application of the chemical. An overhead spray of an aqueous composition of the chemical is applied to the pots at an equivalent rate as indicated below. Two to four sets of plants which received no chemical application are included and serve as controls. All of the pots are maintained under good growing conditions and are watered and are fertilized with a uniform amount of a water-soluble balanced fertilizer. Two weeks after the application of the chemical, the growth responses of the treated plants are compared with that of the control plants. The total height of the plant is measured to the tip of the terminal bud. A variation of 15% in the average total height of the treated plants, when compared to the average total height of the control plants, demonstrate that the chemical is an effective plant growth regulator. Observations made utilizing the test procedure of Example 9 are summarized in Table III.

Table III

| Compounds of Example | RATE Lbs/Acre (kilos/hectare) | Response |
|---|---|---|
| 2 | 0.1 (.112) | Stature reduction, axillary bud development, thick leaf texture, dark foliar color, delayed pod set |
| 4 | .25 (.280) | Stature reduction, leaf distortion, thick leaf texture |
|  | 0.1 (.112) | Stature reduction, thick leaf texture |
|  | .05 (.056) | No response |

In addition to the above responses, compounds of the invention have been shown to increase the seed weight of soybean plants. Effects on yield, being dependent upon the number of seeds per plant, varied.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

The embodiments of the invention in which an exclusive property or privilege is claimed are defined as follows:

1. A method of regulating the growth of leguminous plants which comprises treating said plants with an effective non-lethal amount of a compound having the formula

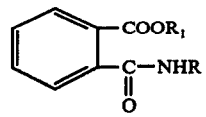

wherein R is pyridyl or pyridyl substituted by halo or alkoxy having from one to four carbon atoms; $R_1$ is hydrogen, lower alkyl and agriculturally acceptable cations.

2. A method according to claim 1 wherein R is pyridyl substituted by halo.

* * * * *